US011690695B2

(12) United States Patent
Nicholas et al.

(10) Patent No.: US 11,690,695 B2
(45) Date of Patent: Jul. 4, 2023

(54) COMPRESSION FORCE SENSOR FOR A HANDHELD ELECTROMECHANICAL SURGICAL SYSTEM

(71) Applicant: Covidien LP, Mansfield, MA (US)

(72) Inventors: David A. Nicholas, Trumbull, CT (US); Brian L. Holden, New Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 98 days.

(21) Appl. No.: 17/342,627

(22) Filed: Jun. 9, 2021

(65) Prior Publication Data

US 2022/0395348 A1    Dec. 15, 2022

(51) Int. Cl.
*A61B 90/00*   (2016.01)
*A61B 17/115*  (2006.01)
*A61B 17/00*   (2006.01)

(52) U.S. Cl.
CPC .......... *A61B 90/06* (2016.02); *A61B 17/1155* (2013.01); *A61B 2017/0003* (2013.01); *A61B 2017/00115* (2013.01); *A61B 2090/065* (2016.02)

(58) Field of Classification Search
CPC ............................. A61B 90/06; A61B 17/1155
See application file for complete search history.

(56) References Cited

U.S. PATENT DOCUMENTS

| 7,303,106 B2 | 12/2007 | Milliman et al. |
| 2006/0273135 A1* | 12/2006 | Beetel .................. A61B 17/128 227/175.1 |
| 2018/0042610 A1* | 2/2018 | Sgroi, Jr. ........... A61B 17/1155 |
| 2019/0200981 A1 | 7/2019 | Harris |
| 2019/0200998 A1* | 7/2019 | Shelton, IV ... A61B 17/320092 |

FOREIGN PATENT DOCUMENTS

EP    3315082 A1    5/2018

OTHER PUBLICATIONS

International Search Report dated Sep. 29, 2022 and Written Opinion completed Sep. 20, 2022 corresponding to counterpart Int'l Patent Application PCT/IB2022/055301.

* cited by examiner

*Primary Examiner* — Nathaniel C Chukwurah
(74) *Attorney, Agent, or Firm* — Carter, DeLuca & Farrell LLP

(57) ABSTRACT

A surgical device includes a tool assembly and a handle assembly. The tool assembly includes a distal portion including a plurality of staples and an anvil assembly movable relative to the distal portion from an open position to a clamped position. The handle assembly includes an approximation mechanism coupled to the anvil assembly and configured to move the anvil assembly from the open position to the clamped position, a force sensor disposed at a distal end of the surgical device, and a controller. The force sensor is configured to sense a change in resistance indicating a force imparted on compressed tissue and on the approximation mechanism. The controller is configured to receive a signal indicative of a force measured by the force sensor and provide an indication of the sensed force.

19 Claims, 8 Drawing Sheets

COMPRESSION FORCE SENSOR FOR A HANDHELD ELECTROMECHANICAL SURGICAL SYSTEM

BACKGROUND

Technical Field

The present disclosure relates to surgical devices. More specifically, the present disclosure relates to handheld electromechanical surgical systems for performing surgical procedures having a force sensor configured to monitor compression forces during tissue clamping, stapling, and/or cutting.

Background of Related Art

Circular stapling devices are used to perform a variety of procedures involving anastomoses in which two tubular anatomical tissue structures are joined together. These procedures include colorectal circular anastomoses, esophageal circular anastomoses, and bariatric circular anastomoses. Typically, a circular stapling device includes a tool assembly and a handle assembly. The tool assembly includes an anvil assembly and a reload that are movable in relation to each other in response to actuation of an approximation mechanism that clamps tissue between the anvil and reload assemblies. The reload includes a staple cartridge, a staple pusher, and an annular knife. The staple cartridge supports one or more annular rows of staples, and the staple pusher is movable within the staple cartridge in response to actuation of a firing mechanism to eject the staples from the staple cartridge into the anvil assembly. The annular knife is positioned radially inward of the annular rows of staples and is movable from a retracted position to an advanced position to cut or core tissue against a cut ring of the anvil assembly.

The circular stapler may be used during an end-to-end anastomosis procedure, during which two portions of a structure (e.g., intestine, colon, etc.) are reconnected, after the diseased tissue is removed. One end of the structure is attached to the anvil, and the opposite end is attached to the staple housing, or cartridge. The two ends of the structure are brought together before creating the anastomosis. Some circular staplers may have a visual gauge that indicates the tissue gap between the anvil and cartridge of the stapler, which displays the distance traveled by the anvil. As the surgeon operates the rotary input mechanism to approximate the anvil to the cartridge, the visual gauge moves into a region that shows it is "safe" to fire the stapler and create the anastomosis. This visual gauge ensures that the stapler is only fired once an appropriate gap has been set. The rotating clamp mechanism also provides beneficial haptic feedback while surgeons are compressing both ends of tissue together. However, both the visual feedback from the gauge and the haptic feedback are subjective and suboptimal. The gauge only factors in distance traveled rather than pressure, and the haptic feedback from the clamping mechanism varies due to broad ranges of surgeon strength and experience. The current system makes it difficult for other surgeons to train because clamping methods are subjective. This leads to circular stapler usage inconsistencies. A continuing need exists for a circular stapling device that has the advantages of monitoring pressure during surgery, avoiding tissue damage due to a fast rate of compression or over compression, and providing feedback to the surgeon.

SUMMARY

This disclosure generally relates to a surgical stapling device for performing procedures involving anastomoses within a body of a patient. The surgical stapling device includes a handle assembly that includes a manually actuated approximation mechanism and a motorized firing mechanism.

In accordance with aspects of the disclosure, a surgical device includes a tool assembly and a handle assembly. The tool assembly includes a distal portion including a plurality of staples and an anvil assembly movable relative to the distal portion from an open position to a clamped position. The handle assembly includes an approximation mechanism coupled to the anvil assembly and configured to move the anvil assembly from the open position to the clamped position, a force sensor disposed at a distal end of the surgical device and configured to sense a change in electrical resistance indicating a compression force imparted on tissue, and a controller configured to receive a signal indicative of a force measured by the force sensor and provide an indication of the sensed force.

In an aspect of the present disclosure, the indication of the force may include visual feedback, haptic feedback, and/or audible feedback based on the measured force.

In another aspect of the present disclosure, the force sensor may include a force sensitive resistor.

In yet another aspect of the present disclosure, the force sensitive resistor may include a substrate including a proximal side and a distal side, a conductive trace deposed on the distal side of the substrate, and a conductive material deposed on the conductive trace.

In a further aspect of the present disclosure, the trace may include an interdigitated pattern.

In yet a further aspect of the present disclosure, the conductive material may include a conductive sheet or a conductive ink.

In an aspect of the present disclosure, the conductive material may include conductive and non-conductive particles suspended in a matrix.

In another aspect of the present disclosure, the controller may be further configured to transmit the indication of the sensed force to a display.

In yet another aspect of the present disclosure, the controller may be further configured to determine if the sensed force is within a force range and provide an indication that clamping forces on the tissue are safe.

In a further aspect of the present disclosure, the distal portion and the anvil assembly may be circular.

In accordance with aspects of the disclosure, a method for providing an indication of force for a surgical device, includes sensing a force measured by a force sensor disposed in the handle assembly of a surgical device. The distal force sensor is configured to sense a change in resistance indicating force between the anvil and cartridge, and informing usage of the approximation mechanism of the surgical device. The method further includes providing an indication of the sensed force during clamping of tissue.

In an aspect of the present disclosure, the method may further include transmitting the indication of the sensed force to a display.

In another aspect of the present disclosure, the method further may include determining if the sensed force is within a force range and providing an indication that it is safe to fire the surgical device.

In yet another aspect of the present disclosure, the indication of the force may include at least one of visual feedback based on the sensed force, haptic feedback, and/or audible feedback based on the sensed force.

In a further aspect of the present disclosure, the force sensor includes a force sensitive resistor.

In accordance with aspects of the disclosure, a force sensor configured to sense a change in resistance indicating a force imparted on an approximation mechanism is presented. The force sensor includes a substantially circular substrate including a proximal side and a distal side, a conductive trace deposed on the distal side of the substrate, and a conductive material deposed on the conductive trace.

In another aspect of the present disclosure, the trace may include an interdigitated pattern.

In yet another aspect of the present disclosure, the conductive material may include a conductive sheet or a conductive ink.

In a further aspect of the present disclosure, the conductive material may include conductive and non-conductive particles suspended in a matrix.

In yet a further aspect of the present disclosure, the conductive material may include a distal side and a proximal side. The force sensor further includes an actuator disk disposed on the distal side of the conductive material.

BRIEF DESCRIPTION OF THE DRAWINGS

Various aspects and features of the disclosure are described with reference to the drawings wherein like numerals designate identical or corresponding elements in each of the several views wherein.

DETAILED DESCRIPTION OF EMBODIMENTS

Figure 1:
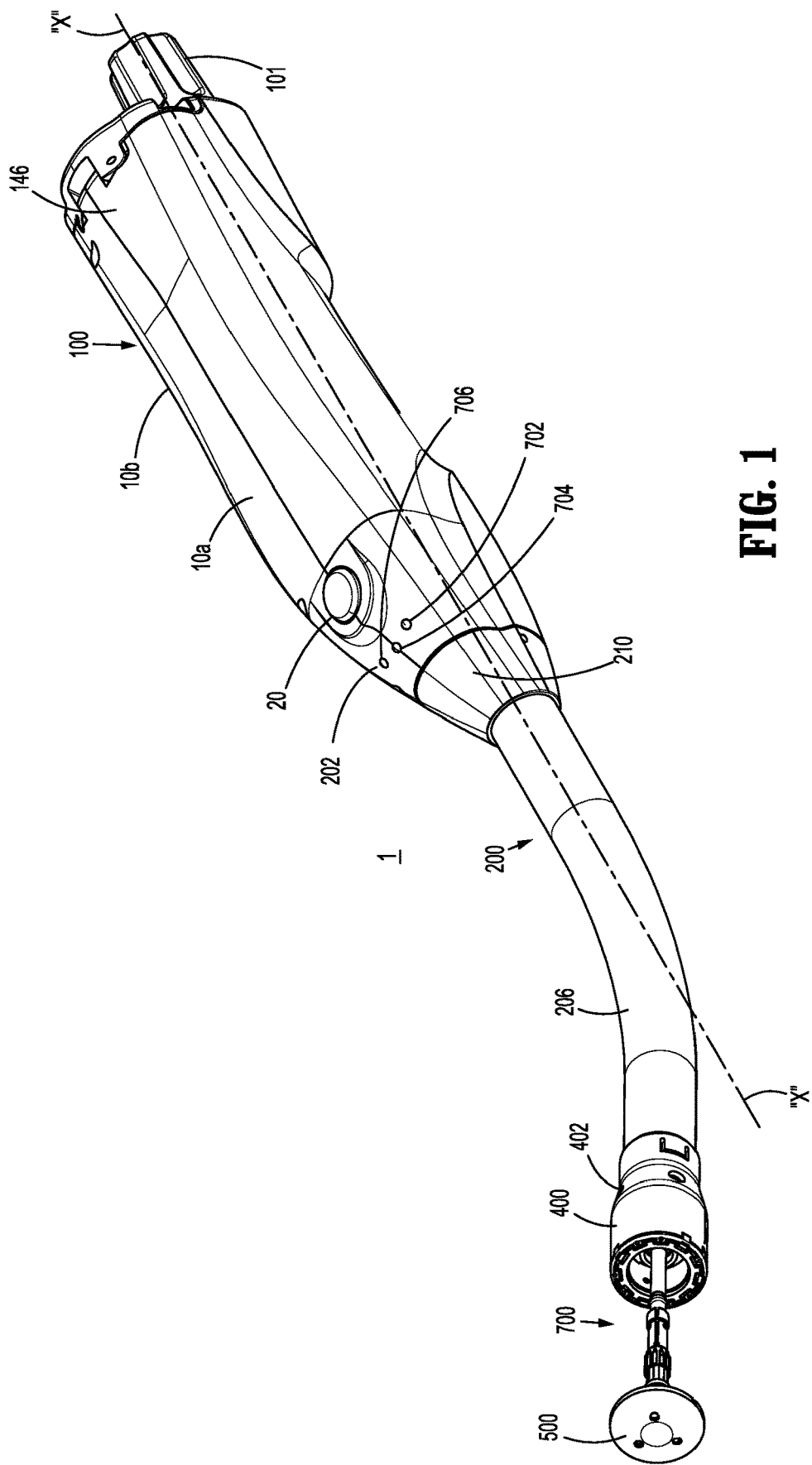
FIG. 1 is a perspective view of a handheld surgical device including a handle assembly, an elongate body, and a tool assembly, according to an embodiment of the present disclosure.

Embodiments of the presently disclosed surgical devices are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

The present disclosure provides a powered circular stapler having a handle assembly, an elongate body coupled to the handle assembly, and a tool assembly coupled to the elongate body. The tool assembly includes an anvil assembly and a cartridge assembly.

The disclosed technology provides feedback to users regarding the pressure that is being applied between the anvil assembly and the cartridge assembly by integrating a force sensor into the circular stapling device to monitor pressure during clamping and providing visual feedback to the user. The disclosed technology ensures users of the stapler do not impose excessive amounts of pressure on the tissue during the clamping phase across all tissue types and tissue thicknesses. This ensures intended device performance during clamp, giving the best result for the patient and the user.

The goal of the feedback is to reduce and/or eliminate the subjectivity of the applied clamp force by providing a consistent indicator of clamp forces across all EEA stapling surgeries. This indicator will provide the surgeon or resident the information needed to prevent exceeding optimal compression forces on tissue during the clamping phase as well as aid in accounting for fluids diffusing out of the staple region to reduce stress on tissue and vasculature.

FIG. 1 illustrates a surgical device 1, such as, for example, a powered circular stapler for forming end-to-end anastomosis ("EEA"), including a handle assembly 100. The surgical device 1 which includes a handle assembly 100, an elongate body 200, and a tool assembly 700. The tool assembly 700 includes an anvil assembly 500 that has an annular staple forming surface (not shown) and a distal portion 400 that has an annular staple cartridge (not shown) that supports staples (not shown). The anvil assembly 500 is supported for movement in relation to the distal portion 400 between an open or unclamped position (FIG. 1) and a clamped position. In aspects of the disclosure, the distal portion 400 includes a proximal portion that is coupled to a distal portion of the elongate body 200 includes a proximal portion that is coupled to the handle assembly 100. It is envisioned that the distal portion 400 can be releasably secured to the elongate body 200 and/or the elongate body 200 can be releasably secured to the handle assembly 100. The distal portion also includes a knife (not shown) that is movable between retracted and advanced positions to cut tissue during an anastomosis procedure.

The surgical device 1 includes a hybrid type handle assembly 100 that includes a manually operated approximation knob 101 for approximating the anvil assembly 500 with the distal portion 400 and a fire button 20 for activating a motor 152 for stapling and cutting tissue. The handle assembly 100 includes a body portion 10b that is ergonomically shaped to be gripped by a clinician. The body portion 10b defines an internal cavity (not shown) and an external recess (not shown). The internal cavity receives drive components of the handle assembly described below. The external recess receives a battery pack that is releasably coupled to the body portion 10b of the handle assembly 100. The approximation knob 101 opens/closes tool assembly 700 (when anvil assembly 500 is connected to the trocar member).

The handle assembly 100 includes a fire button 20 that can be pressed to close a fire switch (not shown) and initiate firing of the surgical device 1, e.g., activate the motor 152 to advance a pusher link and advance the pusher (not shown) to fire staples from the distal portion 400. The fire button 20 may also be illuminated such as a with a light emitting diode (LED). For example, if a safety button (not shown) is pressed, and other necessary conditions are met, the pressing of the safety button (not shown) will arm the surgical device 1, and the fire button 20 will illuminate to provide an indication to a clinician that the surgical device 1 is ready to be fired.

In aspects of the disclosure, the fire button 20 may be configured to blink when the surgical device 1 is coupled to the battery 144 prior to movement of the surgical device 1 to the clamped position.

Figure 2:
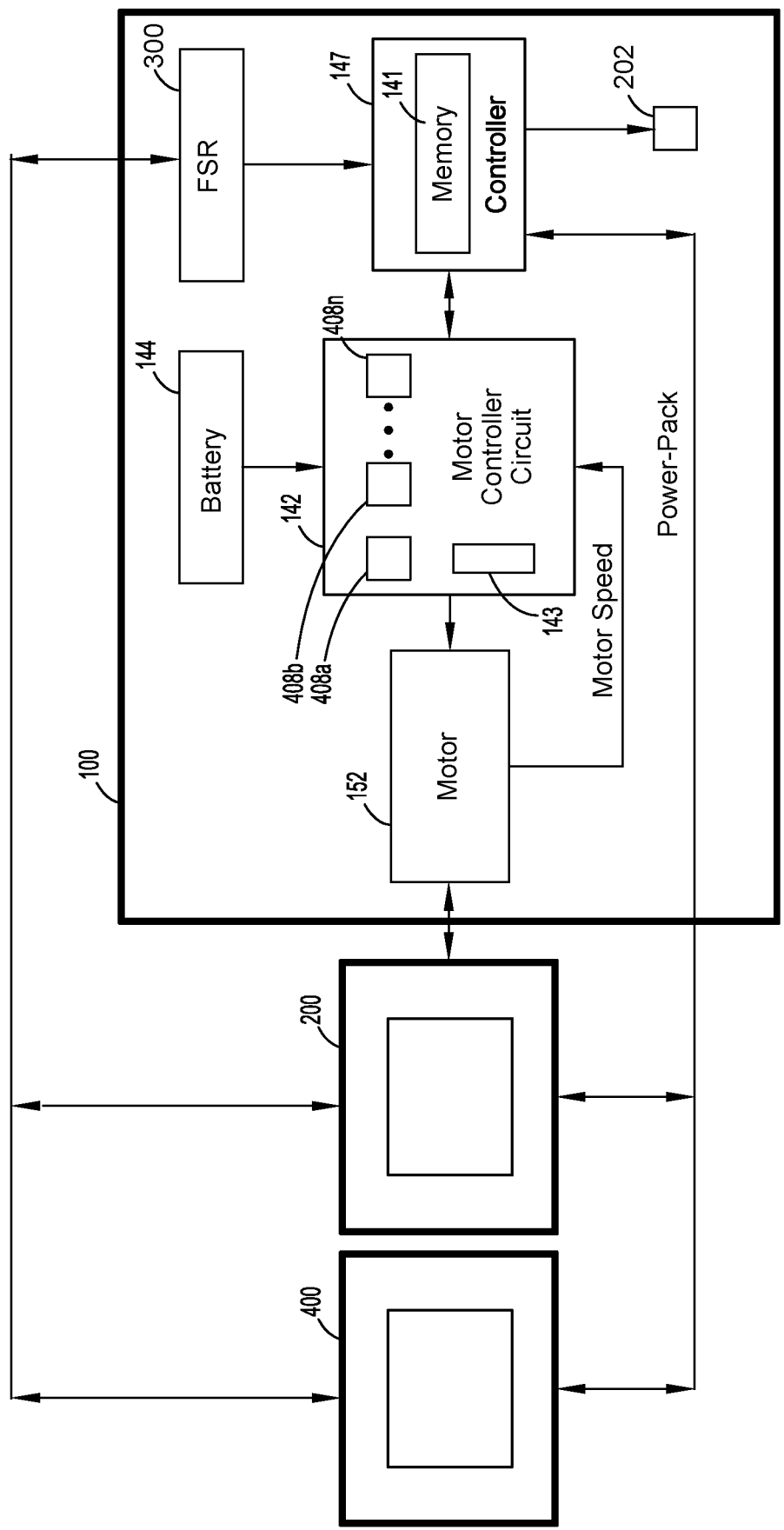
FIG. 2 is a schematic diagram of the handle assembly, the elongate body, and the tool assembly of FIG. 1.

With reference to FIG. 2, the handle assembly 100 includes a controller circuit board 142, a battery 144 configured to supply power to any of the electrical components of handle assembly 100, and a motor 152 coupled to the battery 144. The handle assembly 100 also includes a display 202 (such as LEDs, and/or an OLED display). The controller 147 is coupled to the force sensor 300 of the handle assembly 100 using a wired or a wireless connection and is configured to receive force measurements from the force sensor 300 which are used during operation of the handle assembly 100 to indicate the clamping force on tissue. The controller may further be coupled to the visual indicator 202 to provide a visual indication of the force measurements.

In embodiments, the motor 152 may be coupled to any suitable power source configured to provide electrical energy to the motor 152, such as an AC/DC transformer or a battery. The motor 152 is coupled to a motor controller 143 which controls the operation of the corresponding motor 152, including the flow of electrical energy from the battery 144 to the motor 152. A controller 147 is provided that controls the handle assembly 100. The controller 147 is configured to execute software instructions embodying algorithms disclosed herein, such as clamping, stapling, and cutting algorithms which control operation of the handle assembly 100.

The controller 147 is also coupled to a memory 141. The memory 141 may include volatile (e.g., RAM) and non-volatile storage configured to store data, including software instructions for operating the handle assembly 100.

The handle assembly 100 includes a plurality of motors 152 each including a respective motor shaft (not explicitly shown) extending therefrom and configured to drive a respective transmission assembly. Rotation of the motor shafts by the respective motors function to drive shafts and/or gear components in order to perform the various operations of handle assembly 100, for example cut tissue, or fire staples. In particular, motors 152 of handle assembly 100 are configured to drive shafts and/or gear components in order to selectively extend/retract a firing mechanism (not shown), fire an annular array of staples of distal portion 400, and move an annular knife (not explicitly shown) of distal portion 400.

Figure 3:
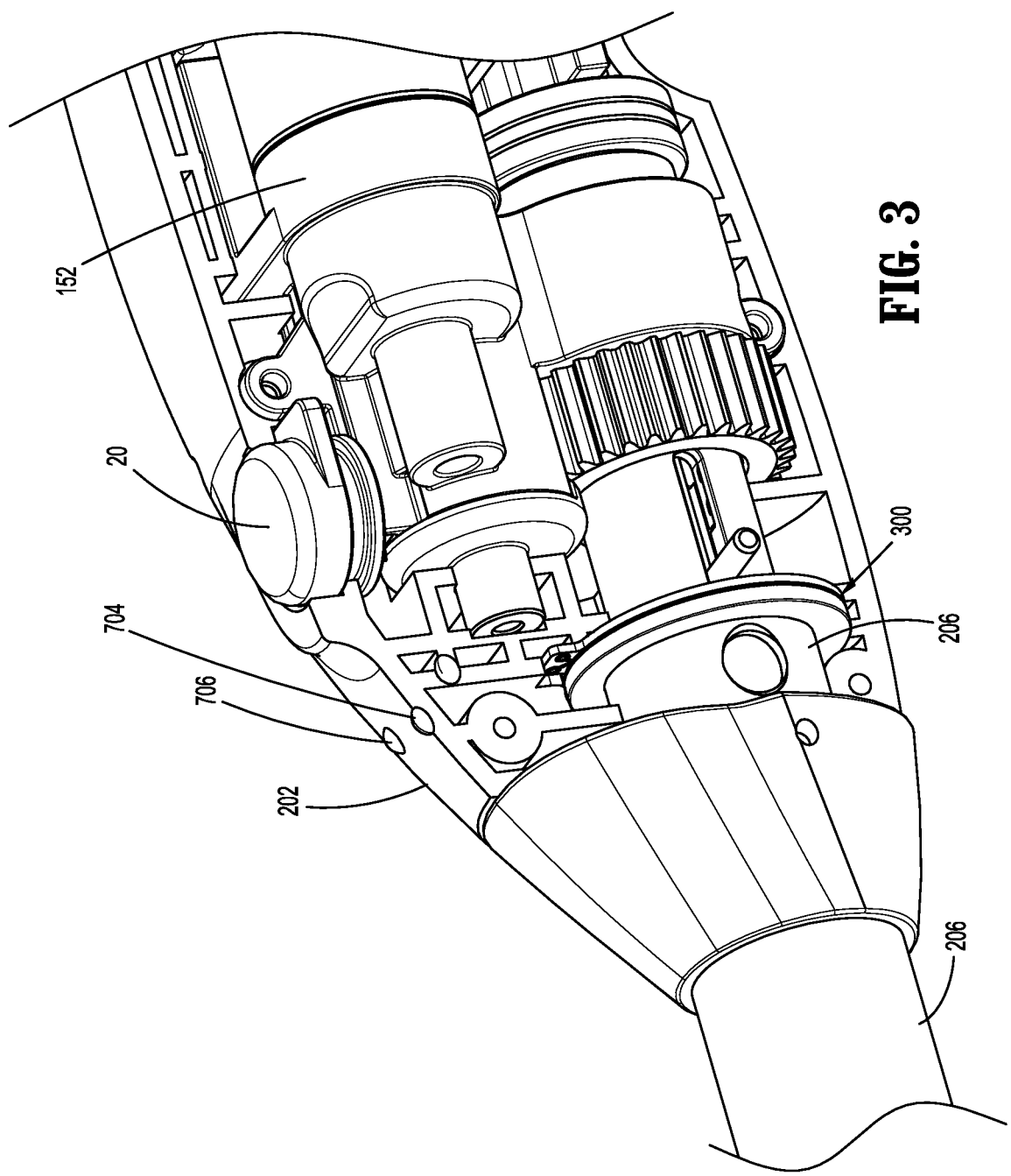
FIG. 3 is a side, cutaway perspective view of the handle assembly including a force sensor, according to an embodiment of the present disclosure.

Turning now to FIG. 3, the handle assembly 100 including a force sensor 300 is shown. The force sensor 300 may be disposed within a distal portion of the handle assembly 100, proximal to outer tube 206. The force sensor 300 is configured to sense force when the outer tube 206 is forced in a proximal direction where the force sensor 300 can sense a force. For example, force may be sensed by the force sensor 300 when clamping, stapling, and/or cutting tissue grasped within the tool assembly 700 (FIG. 1). During clamping, stapling and/or cutting, a reaction force is exerted on anvil assembly 500 and the distal portion 400, which then communicates the reaction force to a force sensitive resistor of the force sensor 300.

Figure 4:
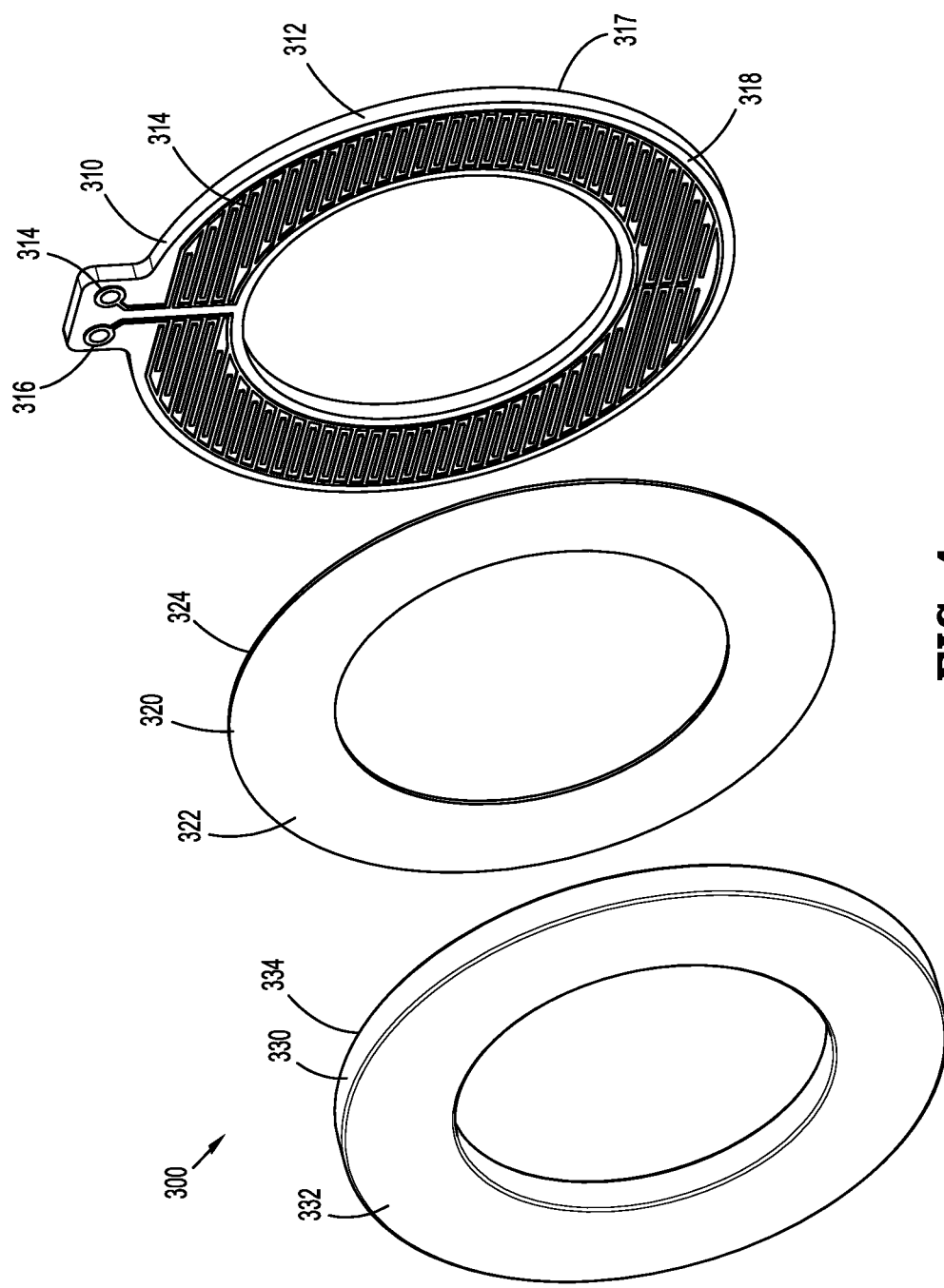
FIG. 4 is an exploded view of a force sensor of FIG. 3.
Figure 5:
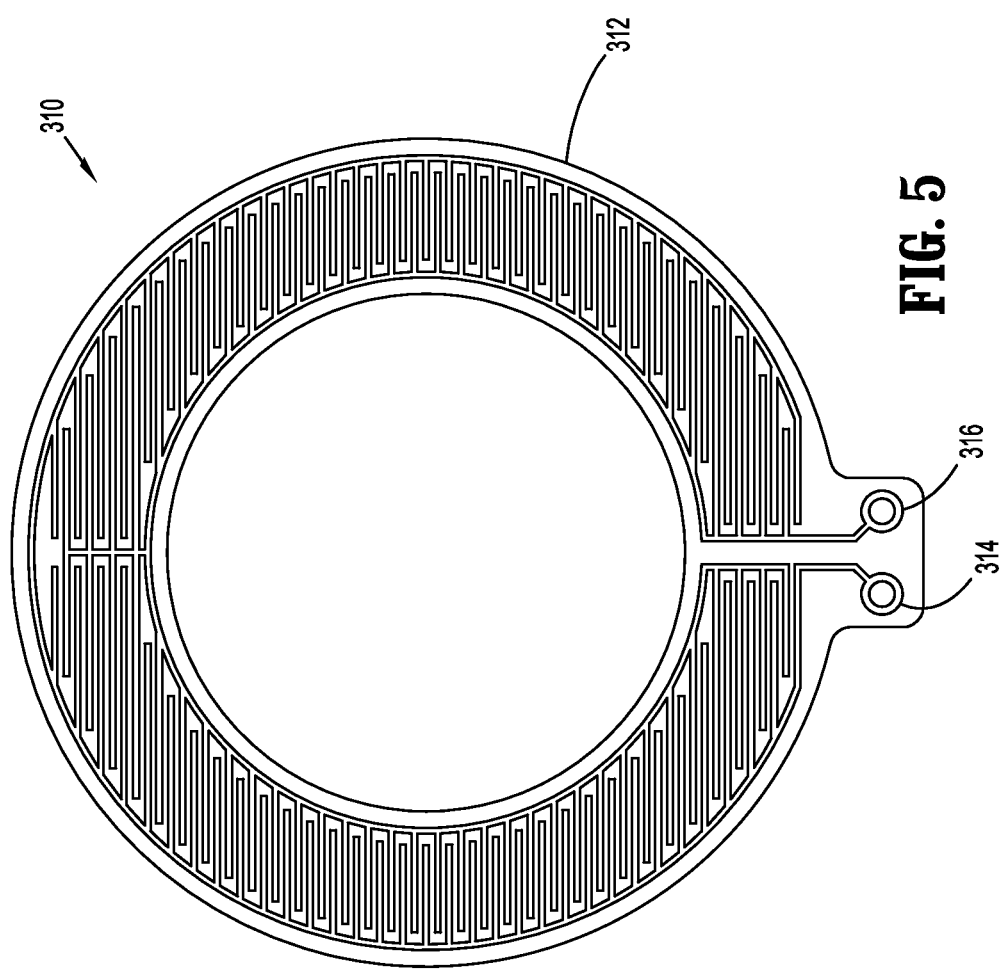
FIG. 5 is a top view of a printed circuit board of the force sensor of FIG. 3.

Referring to FIGS. 4 and 5, the force sensor 300 of the surgical device 1 is shown. The force sensor 300 may be a force sensitive resistor (FSR), also known as a force sensing resistor. A force sensitive resistor is an electrical device whose resistance changes when a force, pressure or mechanical stress is applied. The force sensor 300 functions as a variable resistor whose resistance decreases when the applied force increases. Force may be determined by the controller 147 based on the change in resistance.

The force sensor 300 includes a printed circuit board 310 and a conductive material 320. The printed circuit board 310 generally includes a substrate 312 and a conductive trace 314 (e.g., gold plated copper trace(s)) deposed on the distal side of the substrate 312 The substrate 312 may be made from a suitably flexible material (e.g., a membrane). The conductive trace 314 may include an interdigitated pattern configured to change resistance when pressure is applied to the conductive material 320. The conductive trace 314 includes a first terminal and a second terminal configured for electrical communication with the controller 147. Although shown as a disk, it is contemplated that the force sensor 300 may be any suitable shape (e.g., square, oval, elliptical, etc.).

The conductive material 320 may be a conductive sheet and/or a conductive ink. The conductive material 320 may include conductive and non-conductive particles suspended in a matrix. In aspects, a spacer (not shown) may be disposed between the conductive material 320 and the conductive trace 314.

The conductive material 320 (e.g., a conductive polymer) includes a proximal side 324 disposed on the distal side 318 (on the conductive trace 314) of the printed circuit board 310, and a proximal side 322 configured to engage an actuator disk 330. The actuator disk 330 may be made of a suitably rigid material, such as steel, however, other materials are contemplated.

Figure 6:
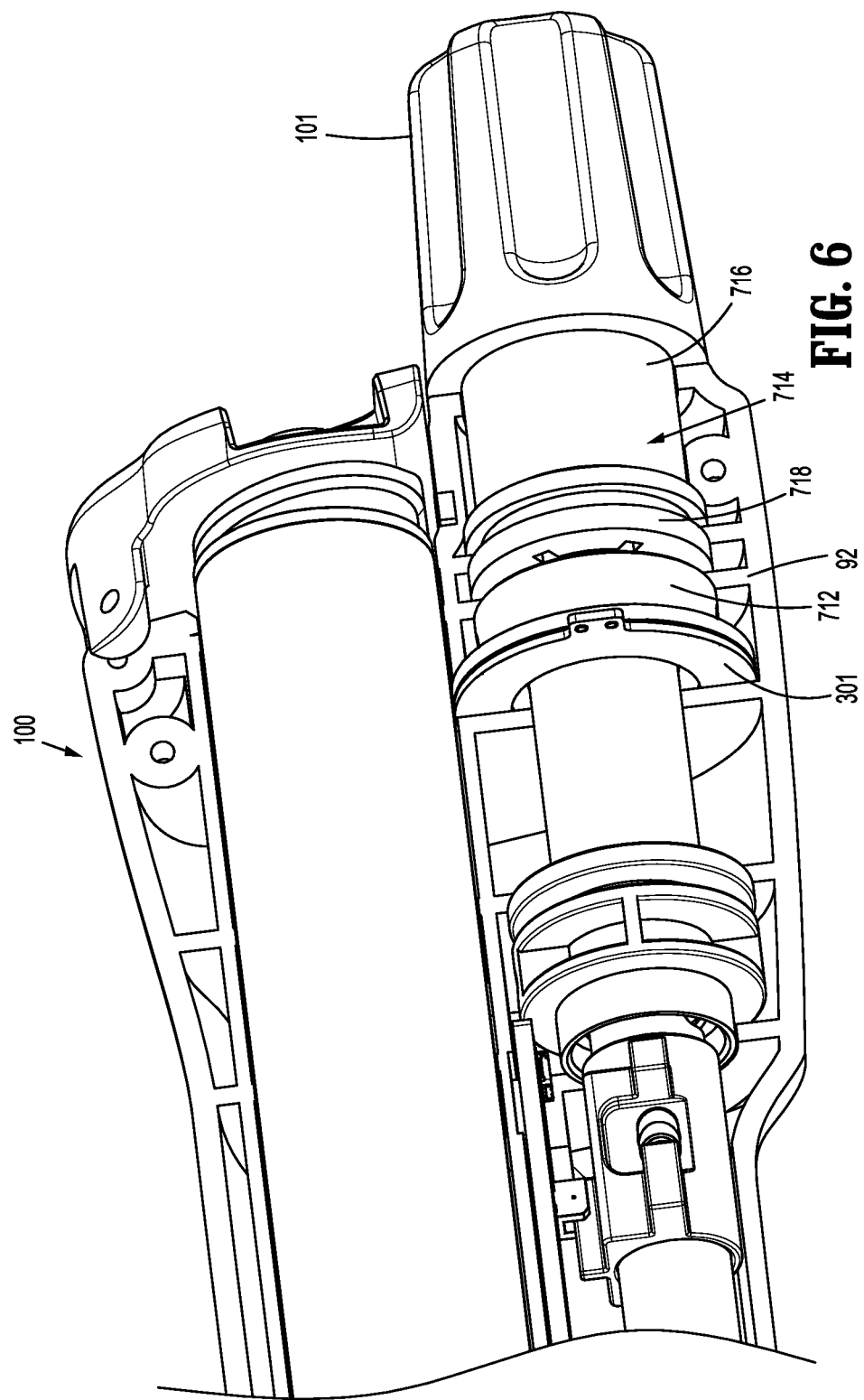
FIG. 6 is a side, cutaway view of the handle assembly of FIG. 1.

With reference to FIG. 6, an alternate proximal location for the force sensor 300 for sensing force when clamping tissue. The proximal force sensor 301 is substantially similar to the more distal force sensor 300. The handle assembly 100 includes a manually operated approximation knob 101 for approximating the anvil assembly 500 with the distal portion 400 and a fire button 20 for activating a motor 152 (FIG. 3) for stapling and cutting tissue. Rotating the approximation knob 101 causes longitudinal movement of the anvil assembly 500 with respect to the distal portion 400.

The handle assembly 100 includes approximation mechanism 714 which includes the approximation knob 101, an anvil clamp screw (not shown), a rotatable sleeve 716, a screw resilient extension (not shown), and an anvil retainer trocar (not shown). The rotatable sleeve 716 includes a cylindrical hollow body portion (not shown) and a cylindrical collar 718 supported on a distal portion of the hollow body portion. The rotatable sleeve 716 defines a longitudinal through bore (not shown). The collar 718 has a diameter greater than the body portion 10b and is received between inwardly extending flanges 92 formed on inner walls of the body portion 10b of the handle assembly 100. Receipt of collar 718 between the flanges 92 axially fixes the rotatable sleeve 716 within the body portion 10b of the handle assembly 100 while permitting rotation of rotatable sleeve 716. It is contemplated that the approximation mechanism 714 may be manually operated or powered.

A proximal portion of the rotatable sleeve 716 extends through an opening (not shown) in the proximal end of the body portion 10b of the handle assembly 100 and is fixedly coupled to the approximation knob 101. The hollow body portion of the rotatable sleeve 716 includes a pair of diametrically opposed ribs (not shown) that are formed on the outer surface of the body portion (not shown) and are received within slots (not shown) defined within the approximation knob 101 to rotatably fix the rotatable sleeve 716 to the approximation knob 101 such that rotation of the approximation knob 101 causes concurrent rotation of rotatable sleeve 716.

Rotation of the approximation knob 101 moves the anvil assembly 500 in relation to the distal portion 400 between the open and clamped positions. U.S. Pat. No. 7,303,106 describes a stapling device including an anvil assembly 500 and anvil retainer that are releasably coupled together and are suitable for use with the surgical device 1.

The force sensor 300 may be disposed within the handle assembly 100, proximal to the cylindrical collar 708. The force sensor 300 is configured to sense force when the cylindrical collar 708 is forced in a proximal direction where the force sensor 300 can sense a force. For example, force may be sensed by the force sensor 300 when clamping tissue grasped within the tool assembly 700 (FIG. 1). It is contemplated that a force sensor 300 may be used to sense force when stapling and cutting issue.

For further details regarding the construction and operation of the circular stapler and its components, reference may be made to U.S. Application No. 63/140,066, filed on Jan. 21, 2021, the entire contents of which being incorporated by reference herein.

Figure 7:
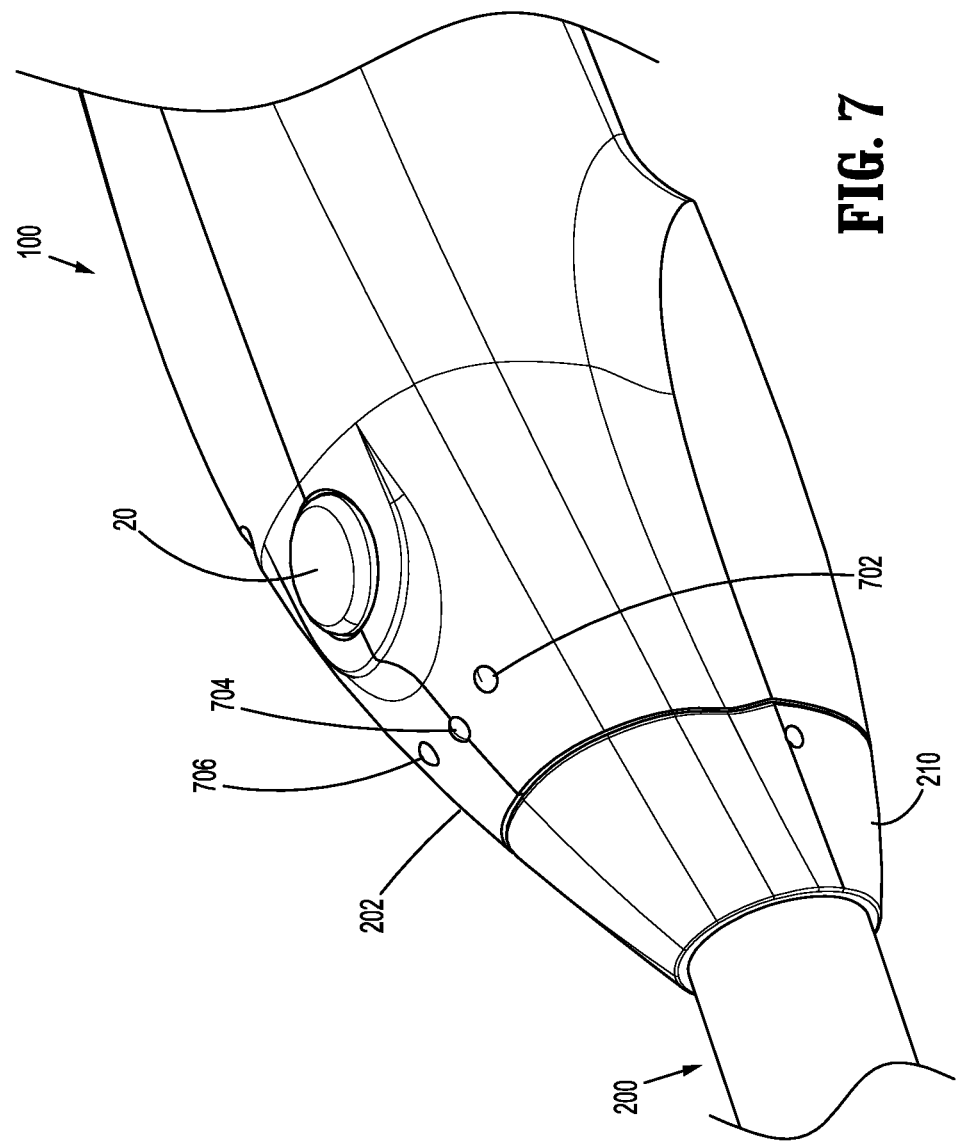
FIG. 7 is a perspective view of the handle assembly of FIG. 1, including a visual indicator, according to an embodiment of the present disclosure.

FIG. 7 shows a perspective view of the handle assembly 100 of FIG. 1, including a visual indicator 202 (e.g., visual feedback). The handle assembly 100 may include visual indicators 202 for providing visual feedback to the user to indicate how much force the user is applying during tissue clamping. This indication may complement haptic feedback provided by the manually controlled approximation knob 101. In aspects, the visual indicator 202 may include one or more LEDs 702, 704, 706 (e.g., a green and red light, a green/yellow/red light system, and/or a multi-color light), an OLED display, an LED display, and/or a series of flashing lights. An additional benefit of implementing visual feedback is that the lights and/or screen can be visible to both surgeons and residents, thereby creating potential to be a training tool for streamlined EEA clamping.

The visual feedback may include a series of lights (colors or flashing patterns) where it will be clear whether the surgeon is in a low force or high force range of applied force.

Figure 8:
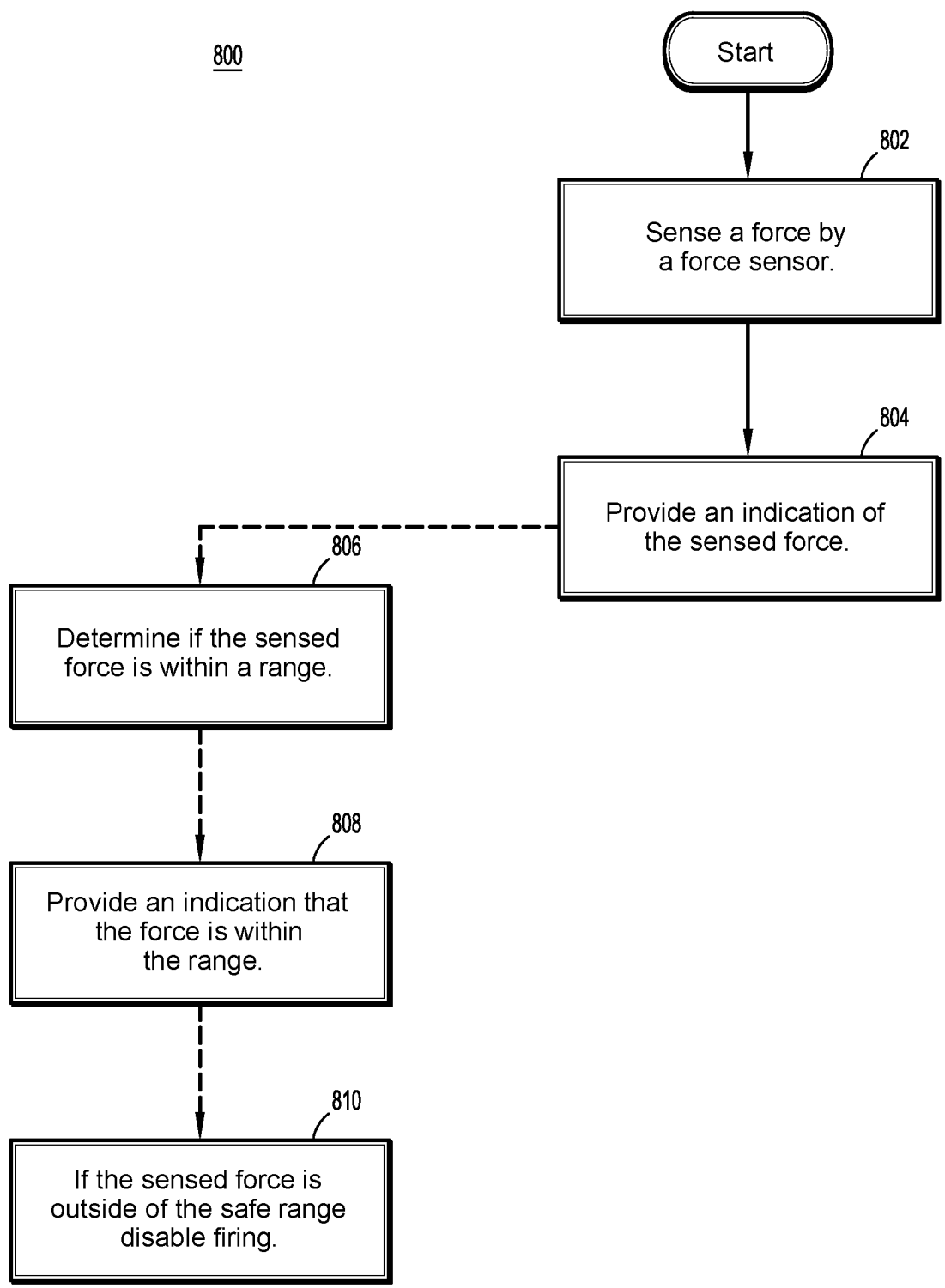
FIG. 8 is a method for controlling the surgical device of FIG. 1 during the stapling sequence according to an embodiment of the present disclosure.

With reference to FIG. 8, which shows a method for providing an indication of force for a surgical device, during clamping, as the approximation knob 101 advances the anvil assembly 500, the controller 147 continually monitors the force measured by the force sensor 300.

Initially at step 802, when the clinician operates the approximation knob 101 of the circular stapler, a controller of the circular stapler monitors the force from a force sensor 300 disposed in the handle assembly 100 disposed on the proximal end of the outer tube 206. The force sensor 300 includes a force sensitive resistor and/or a strain gauge. It is contemplated that an optional second force sensor (e.g., a proximal force sensor 300 FIG. 6) may be used to additionally monitor stapling force at a second location in the surgical device 1, thus allowing for additional accuracy. In aspects, the force sensor 300 may be located at the proximal portion of handle assembly (FIG. 3) or the distal portion of the handle assembly (FIG. 6) of the stapling device 1.

Next, at step 804, the controller 147 provides an indication of the sensed force. For example, the indication of the force may include visual feedback (e.g., LEDs or a display) based on the sensed force, audible feedback (e.g., a beep, or a voice), and/or additional haptic feedback (e.g., by a motor vibrating the handle to indicate the sensed force) based on the sensed force. For example, the surgical device 1 may include three separate color LEDs and/or a multicolor LED.

Next, at step 806, the controller 147 may determine if the sensed force is within a force range, for example about 100 to about 150 lbs. The force range may include a range from a set of predetermined ranges between 0 and about 250 lbs. (e.g., 0-50, 50-100, 100-150, etc.). The controller 147 may blink the LEDs, where LED colors indicate a force within a predetermined range. In aspects, the compared force may be used to determine if the force is within the predetermined force range. The indication of the sensed force will guide the clinician to the middle of the force range.

Next, at step 808, the controller 147 may provide an indication that the force is within the force range. For example, the user may see a series of lights as indicators of force being applied during clamp. This system suggests that unwanted levels of tissue compression are not occurring during the clamping phase of the surgical device 1. When this force is reduced there can be higher confidence that integrity of the tissue vasculature and structure has not been compromised. The combined force sensitive and feedback system can improve circular stapling operations during EEA.

In aspects, controller 147 may output a visual warning message to the user to slow down clamping speed and allow tissue to relax before proceeding. For example, the controller 147 may light the center LED 706 green.

After the stapling sequence is completed, the user presses the fire button 20 to commence the stapling sequence, cut the stapled and compressed tissue, and form the anastomosis.

Next, at step 810, the controller 147 may determine that the sensed force is out of the safe range and disable firing.

During the stapling procedure, users rotate the approximation knob 101 until a gauge on the surgical device indicates that the gap between the anvil assembly 500 and cartridge is in a safe region to fire and that an internal range switch (not shown) is activated. In addition to tactile feedback, the visual feedback provided by the visual indicators 202 allow for surgeons to understand the magnitude of the force they are applying to the tissue. Thus, a user can ensure that there is enough time for interstitial fluids to leave the stapling site, thereby avoiding increased force during clamp. When the clamp speed is reduced, so is the force imparted by the anvil assembly 500. The force sensor 300 and visual feedback will ensure that users are aware of the force they are applying during clamp and enable safe stapling practice in terms of manual clamping across all surgeons. Less stress on the stapled tissue and vasculature is important for there to be greater perfusion to the staple line post anastomosis. Greater perfusion can lead to improved healing.

In aspects, the controller 147 may provide an indication that it is safe to fire the surgical device. In aspects, a subsequent switch (not shown) may be used to ensure the device has been clamped to an appropriate gap. A force too low can indicate the device should not be fired as it indicates no anvil attached.

Since the controller 147 monitors the force sensor 300 in real time, it is contemplated that the controller 147 may continuously adjust the motor 152 output to achieve a target stroke.

In aspects, the controller 147 may calculate a difference between a first measurement of the distal force sensor 300 and a second measurement of the proximal force sensor 301. The controller 147 may perform a comparison of the first and second force to improve the accuracy of the force measurement. In aspects, if the measured force is above the maximum stapling force, which may be about 250 lbs., the controller 147 disables firing and displays a sequence on the display 146 instructing the user the steps to exit the stapling sequence.

In aspects, the distal portion 400 (FIG. 1) may use a replaceable reload which includes a storage device 402 configured to store operating parameters of the reload 400 including starting clamping force, maximum clamping force, a force factor, and the like. Each type of reload 400 may have a corresponding starting clamping force, which the controller 147 may obtain automatically by reading the starting clamping force value from the storage device 402 and/or set manually by the user by selecting either the type of the reload or the clamping force directly. Starting clamping force may be any suitable threshold from about 100 pounds to about 200 pounds, in embodiments, the target clamping force may be approximately 150 pounds. For example, a 33 mm sized reload 400 may have a clamping force of about 150 lbs.

Although circular stapling devices have been used as examples, the disclosed technology may be used with linear stapling instruments.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
    a tool assembly including:
        a distal portion including a plurality of staples; and
        an anvil assembly being movable relative to the distal portion from an open position to a clamped position;
    a handle assembly including:
        an approximation mechanism coupled to the anvil assembly and configured to move the anvil assembly from the open position to the clamped position;
    a force sensor disposed at a distal end of the surgical device, the force sensor configured to sense a change in electrical resistance indicating a compression force on tissue, wherein the force sensor includes:
        a substantially circular substrate including a proximal side and a distal side;
        a conductive trace disposed on the distal side of the substrate; and
        a conductive material disposed on the conductive trace; and
    a controller configured to:
        receive a signal indicative of a force measured by the force sensor; and
        provide an indication of the sensed force.

2. The surgical device according to claim 1, wherein the indication of the force includes at least one of visual feedback, haptic feedback, or audible feedback based on the measured force.

3. The surgical device according to claim 1, wherein the distal force sensor includes a force sensitive resistor.

4. The surgical device according to claim 1, wherein the trace includes an interdigitated pattern.

5. The surgical device according to claim 1, wherein the conductive material includes a conductive sheet or a conductive ink.

6. The surgical device according to claim 1, wherein the conductive material includes conductive and non-conductive particles suspended in a matrix.

7. The surgical device according to claim 1, wherein the controller is further configured to:
    transmit the indication of the sensed force to a display.

8. The surgical device according to claim 1, wherein the controller is further configured to:
    determine if the sensed force is within a force range; and
    provide an indication that compression forces on the tissue are within a predetermined range.

9. The surgical device according to claim 1, wherein the distal portion and the anvil assembly are circular.

10. A method for providing an indication of force for a surgical device, the method comprising:
    sensing a force measured by a distal force sensor disposed at a distal end of a surgical device, the distal force sensor configured to sense a change in resistance indicating a force imparted on an approximation mechanism of the surgical device, wherein the distal force sensor includes:
    a substantially circular substrate including a proximal side and a distal side;
    a conductive trace disposed on the distal side of the substrate; and
    a conductive material disposed on the conductive trace; and
    providing an indication of the sensed force during clamping tissue.

11. The method according to claim 10, further comprising transmitting the indication of the sensed force to a display.

12. The method according to claim 10, further comprising:
    determining if the sensed force is within a force range; and
    providing an indication that compression forces on the tissue are within a predetermined range.

13. The method according to claim 10, wherein the indication of the force includes at least one of visual feedback based on the sensed force, haptic feedback, or audible feedback based on the sensed force.

14. The method according to claim 10, wherein the force sensor includes a force sensitive resistor.

15. A force sensor configured to sense a change in resistance indicating a force imparted on an approximation mechanism, the force sensor comprising:
    a substantially circular substrate including a proximal side and a distal side;
    a conductive trace disposed on the distal side of the substrate; and
    a conductive material disposed on the conductive trace.

16. The force sensor according to claim 15, wherein the trace includes an interdigitated pattern.

17. The force sensor according to claim 15, wherein the conductive material includes a conductive sheet or a conductive ink.

18. The force sensor according to claim 15, wherein the conductive material includes conductive and non-conductive particles suspended in a matrix.

19. The force sensor according to claim 15, wherein the conductive material includes a distal side and a proximal side, and
   wherein the force sensor further includes an actuator disk disposed on the distal side of the conductive material.

\* \* \* \* \*